(12) United States Patent
Kim et al.

(10) Patent No.: US 11,000,039 B2
(45) Date of Patent: *May 11, 2021

(54) COMPOSITION FOR CONTROLLING NEMATODE COMPRISING GRAMMICIN COMPOUND AS EFFECTIVE INGREDIENT AND USES THEREOF

(71) Applicants: INDUSTRY FOUNDATION OF CHONNAM NATIONAL UNIVERSITY, Gwangju (KR); NATIONAL INSTITUTE OF BIOLOGICAL RESOURCES, Incheon (KR)

(72) Inventors: Jin-Cheol Kim, Gwangju (KR); Tae Yoon Kim, Daegu (KR); Ja Yeong Jang, Jeollabuk-do (KR); Won-Jae Chi, Gyeonggi-do (KR); Chang Hwan Bae, Gyeonggi-do (KR); Joo Hong Yeo, Gyeonggi-do (KR)

(73) Assignees: INDUSTRY FOUNDATION OF CHONNAM NATIONAL UNIVERSITY, Gwangju (KR); NATIONAL INSTITUTE OF BIOLOGICAL RESOURCES, Incheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/336,336

(22) PCT Filed: Sep. 27, 2017

(86) PCT No.: PCT/KR2017/010666
§ 371 (c)(1),
(2) Date: Mar. 25, 2019

(87) PCT Pub. No.: WO2018/062823
PCT Pub. Date: Apr. 5, 2018

(65) Prior Publication Data
US 2020/0022371 A1    Jan. 23, 2020

(30) Foreign Application Priority Data

Sep. 29, 2016 (KR) .......................... 10-2016-0125514

(51) Int. Cl.
| | |
|---|---|
| A01N 43/90 | (2006.01) |
| A01N 63/30 | (2020.01) |
| A01G 7/06 | (2006.01) |
| A01N 25/04 | (2006.01) |
| A01N 25/14 | (2006.01) |
| A01N 43/54 | (2006.01) |
| A01N 57/14 | (2006.01) |
| C12P 17/18 | (2006.01) |

(52) U.S. Cl.
CPC ............... *A01N 43/90* (2013.01); *A01G 7/06* (2013.01); *A01N 25/04* (2013.01); *A01N 25/14* (2013.01); *A01N 43/54* (2013.01); *A01N 57/14* (2013.01); *A01N 63/30* (2020.01); *C12P 17/181* (2013.01)

(58) Field of Classification Search
CPC ....................................................... A01N 43/90
See application file for complete search history.

(56) References Cited

U.S. PATENT DOCUMENTS

2014/0005235 A1    1/2014 Jung et al.

FOREIGN PATENT DOCUMENTS

| KR | 10-2005-0119800 A | 12/2005 |
|---|---|---|
| KR | 10-2009-0111514 A | 10/2009 |
| KR | 10-1144987 B1 | 5/2012 |
| KR | 10-1501033 B1 | 3/2015 |

OTHER PUBLICATIONS

Kim et al., Pest Manag. Sci., 2018, 74, p. 384-391, Accepted article published: Aug. 29, 2017 (Year: 2017).*
Holden-Dye et al., Anthelmintic drugs and nematicides: studies in Caenorhabditis elegans (Dec. 16, 2014), WormBook, ed. The C. elegans Research Community, WormBook, doi/10.1895/wormbook.1.143.2, http://www.wormbook.org, 29 pages (Year: 2014).*
Sureew An Mekkamol, "Endophytic Fungi of *Tectona grandis* L. (Teak) Sureew an Mekkamol", Jan. 1, 1998.
European Search Report For EP 17856709 dated Feb. 20, 2020 from European patent office in a counterpart European patent application.
International Search Report for PCT/KR2017/010666 dated Feb. 19, 2018.
Edwards. R. L. et al., "Metabolites of the Higher Fungi. Part 33. Grammicin, a Novel Bicyciic C7H6O4 Furanopyranol from the Fungus Xylaria Grammica (Mont.) Fr.", Journal of the Chemical Society, Perkin Transactions, pp. 1296-1299, 2001.
Kim, T. Y et al., "Nematicidal Activity of Grammicin Produced by Xylaria Grammica KCTC 13121BP Against Meloidogyne Incognita", International Symposium and Annual Meeting of the KSABC, article No. S5-5, p. 114, 2017.
Guohong Li et al., "Nematicidal Substances from Fungi", Recent Patents on Biotechnology, vol. 1(2), 2007.

* cited by examiner

*Primary Examiner* — Jonathan S Lau
(74) *Attorney, Agent, or Firm* — The PL Law Group, PLLC (57) ABSTRACT

A method for controlling nematode includes treating a plant or soil with a composition comprising a grammicin compound of Formula 1 or an agriculturally acceptable salt thereof. The grammicin compound may be isolated from a *Xylaria grammica* strain so that it is harmless to a human body, does not cause any environmental contamination, and exhibits an excellent control activity against root knot nematodes. Thus, it can be advantageously used for developing an environment-friendly natural nematicide and production of a high value-added organic agricultural product.

9 Claims, 7 Drawing Sheets

COMPOSITION FOR CONTROLLING NEMATODE COMPRISING GRAMMICIN COMPOUND AS EFFECTIVE INGREDIENT AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/010666 filed on Sep. 27, 2017, which claims priority to the benefit of Korean Patent Application No. 10-2016-0125514 filed in the Korean Intellectual Property Office on Sep. 29, 2016, the entire contents of which are incorporated herein by reference.

TECHNICAL FIELD

The present invention relates to a composition for controlling nematode comprising grammicin compound isolated from *Xylaria grammica* strain as an effective ingredient, and uses thereof.

BACKGROUND ART

Plant parasitic nematodes are pest which mainly occurs in large amount in successive cropping areas and causes a huge damage on crops, and they bring a yearly loss of 78 trillion dollars all over the world. There are thousand kinds of plant parasitic nematodes belonging to *Platyhelminthes*, and, depending on eating method, shape, and parasitic mode, they are classified into root knot nematode (*Meloidogyne* spp.), root-lesion nematode (*Paratylenchus* spp.), stunt nematode (*Tylenchorhynchus* spp.), pin nematode (*Paratylenchus* spp.), ring nematode (*Criconemoides* spp.), spiral nematode (*Hellicotylenchus* spp.), cyst nematode (*Heterodera* spp.), stem nematode (*Ditylenchus* spp.), and leaf nematode (*Ahelenchoides* spp.).

In a culture field of greenhouse horticulture in South Korea, crop yield reduction of about 30 to 40% is caused every year by infection with root knot nematodes (e.g., about 85% of Seongju farms are infected by root knot nematode), and the root knot nematodes cause a damage on almost every greenhouse horticultural crop in South Korea (e.g., cucumber, watermelon, Korean melon, tomato, and the like).

The root knot nematode (*Meloidogyne* spp.) was first found in 1850s from root knot of cucumber grown in British greenhouse, and it is established as *Meloidogyne* sp. by Chitwood in 1949. Over the world, 78 types of root knot nematode are present. In South Korea, 6 types of root knot nematode are present, and, among them, the root knot nematodes considered to be the biggest problem in culture field of South Korea are 3 types, i.e., *Meloidogyne arenaria* (peanut root knot nematode), *Meloidogyne hapla* (carrot root knot nematode), and *Meloidogyne incognita* (sweet potato root knot nematode). Those nematodes have various crops as a host, i.e., eggplant, potato, hot pepper, tobacco, carrot, strawberry, peanut, radish, pear, lettuce, watermelon, spinach, onion, cucumber, burdock, ginseng, peony, sesame, Korean melon, bean, tomato, grape, and pumpkin.

The damage caused by root knot nematodes is shown all over the world, and the damage is particularly strong in the tropical or sub-tropical region with high mating number of nematodes due to higher temperature compared to the cold region. In South Korea, because vegetables are cultivated all year long including winter season by using facilities, sweet potato root knot nematode (*M. incognita*) and peanut root knot nematode (*M. arenaria*) adapted to sub-tropical region occur more intensely.

The plant parasitic nematodes exhibit a very significant damage such that is referred to as a source of all diseases in agricultural crops. Once any area is infected by a plant parasitic nematode, it is almost impossible to have complete control. Meanwhile, as a method for reducing this damage caused by nematodes, there are crop rotation, soil dressing, sunlight sterilization, treatment with fresh water, soil fuming, treatment with nematicide, or the like. However, since the soil-infecting nematodes like root knot nematode spend most of their lives in soil and form a resistant body that can endure harmful environments in soil, it is difficult to have effective control only by cultivation control like crop rotation and field rotation. For the nematode control, a pesticide easily obtainable by organic synthesis has been mainly used until now. However, as harmful influences exhibited by a pesticide obtained by organic synthesis on human body and natural environment are known in recent years, registration of highly effective nematicides like aldicarb, fenamiphos, methyl bromide, dibromochloropropane, and EDB (ethylenedibromide) is cancelled, and thus a method for replacing those pesticides is strongly demanded.

As a method for environment-friendly control of plant parasitic nematodes, there is a method of using microbes or a method of using metabolites produced by microbes. By having various metabolic pathways, fungi are able to synthesize various metabolites, and it is known that many antibiotics and various commercially useful products are produced by fungi. As such, it is believed that the secondary metabolites produced by fungi may have a nematicidal activity.

Meanwhile, in Korean Patent Registration No. 0574348, "*Xylaria* sp. AH001 strain producing griseofulvin, formulation for controlling plant diseases containing same, and method for controlling plant diseases by using same" is disclosed, and in Korean Patent Registration No. 1144987, "Culture product of *Chryseobacterium* sp. FBF-7 and composition for controlling root know nematode comprising the same" is disclosed. However, nothing has been described with regard to "composition for controlling nematode comprising grammicin compound isolated from *Xylaria grammica* strain as an effective ingredient, and uses thereof", as they are disclosed in the present invention.

SUMMARY

The present invention is devised under the circumstances described above, and, according to the present invention, the nematicidal activity was examined by using a culture filtrate of various fungi, and, as a result, it was found that the culture filtrate of *Xylaria grammica* strain exhibits a potent nematicidal activity, and thus a novel active compound was isolated and identified.

According to the experiments of the present invention, the ethyl acetate layer fractionated from a culture filtrate of *Xylaria grammica* of the present invention and grammicin isolated in pure form from the ethyl acetate layer were confirmed to have a mortality against $2^{nd}$ stage juveniles of sweet potato root knot nematode (*M. incognita*) and an activity of suppressing egg hatching. It was also confirmed that grammicin has a mortality against $2^{nd}$ stage juveniles of carrot root knot nematode (*M. hapla*).

Presently, grammicin exhibits a higher activity than trans-cinnamaldehyde which is frequently used in environment-friendly agriculture. Furthermore, it exhibits a biological activity that is completely different from patulin, which is an isomer of grammicin and known as a mycotoxin. Namely, while patulin exhibits high cytotoxicity for colon cancer cells, grammicin exhibits no toxicity at a test concentration. On the other hand, while grammicin has a very high mortality against root knot nematodes, patulin has almost no activity.

Accordingly, the present invention can be used, instead of a current method for chemical control of nematodes, as a method for biological control of nematodes as it is harmless to a human body and natural environment. Furthermore, as it is confirmed that a new use of grammicin for environment-friendly control of nematode control, which is more excellent in terms of nematode control, can be provided, the present invention is completed accordingly.

To achieve the object described above, the present invention provides a composition for controlling nematode comprising, as an effective ingredient, grammicin compound or a salt thereof.

Furthermore, the present invention provides a method for controlling nematode by treating a plant or soil with the composition for controlling nematode.

Still furthermore, the present invention provides a method for producing a grammicin compound including carrying out stationary culture of a *Xylaria grammica* strain in PDB (potato dextrose broth) medium containing 4 to 23 g/l glucose.

Because grammicin as a compound for controlling nematode according to the present invention is derived from a natural product, it is harmless to a human body, does not cause any environmental contamination, and exhibits an excellent control activity against root knot nematodes, and thus it can be advantageously used for developing an environment-friendly natural nematicide and producing a high value-added organic agricultural product.

Furthermore, grammicin can be utilized either directly or as a lead compound for developing a chemical for controlling nematode in animal and human. If this technique is developed and transferred to domestic companies to yield production of a biological control product, it can contribute not only to the domestic production of environment-friendly agricultural products but also earning of foreign currencies according to export of the technique to the global market.

DETAILED DESCRIPTION

To achieve the object described above, the present invention provides a composition for controlling nematode comprising, as an effective ingredient, a grammicin compound of the following chemical formula 1 or a salt thereof.

[Chemical formula 1]

The grammicin compound of the present invention may be a compound which has been isolated from a *Xylaria grammica* strain. It is preferably a compound isolated from the *Xylaria grammica* strain with deposition number of KCTC13121BP, more preferably a compound isolated from a culture broth of *Xylaria grammica* strain, and most preferably a compound isolated from an ethyl acetate fraction of a culture solution of a *Xylaria grammica* strain, but it is not limited thereto. The *Xylaria grammica* strain was deposited in the Korea Research Institute of Bioscience and Biotechnology (having the address of 181, Ipsin-gil, Jeongeup-si, Jeolllabuk-do 56212, Republic of Korea under the Access number of KCTC 13121BP on Sep. 28, 2016. The deposit has been made under the terms of the Budapest Treaty and all restrictions imposed by the depositor on the availability to the public of the biological material will be irrevocably removed upon the granting of a patent.

The grammicin compound represented by the above chemical formula 1 can be isolated and purified from a culture solution of a *Xylaria grammica* strain, or chemically synthesized. As for the method for chemical synthesis of the above compound, a method generally known in the field can be used.

With regard to the composition for controlling nematode according to the present invention, the nematodes are preferably root knot nematode (*Meloidogyne* sp.), and the root knot nematode (*Meloidogyne* spp.) may be more preferably sweet potato root knot nematode (*Meloidogyne incognita*), carrot root knot nematode (*Meloidogyne hapla*), Java root knot nematode (*Meloidogyne javanica*), peanut root knot nematode (*Meloidogyne arenaria*) or tomato root knot nematode (*Meloidogyne incognita*), and most preferably sweet potato root knot nematode (*Meloidogyne incognita*) or carrot root knot nematode (*Meloidogyne hapla*) strain, but it is not limited thereto.

The composition for controlling nematode of the present invention may additionally contain a nematicidally active compound and a compound for having induced resistance. Examples of the nematicidally active compound include an avermectin-based nematicidally active compound, morantel tartrate, mesulfenfos, and levamisol, but it is not limited thereto.

Examples of the avermectin-based nematicidally active compound include emamectin benzoate, abamectin, milbemectin, and ivermectin, but is it not limited thereto.

Examples of the compound for having induced resistance include acibenzolar-S-methyl, salicylic acid, and jasmonic acid, but it is not limited thereto.

The composition for controlling nematode of the present invention may additionally contain a compound which is contained in a typically-used nematicidal agent, and it may contain, as a vehicle other than the aforementioned effective ingredient, agrochemically acceptable solid carrier, liquid carrier, liquid diluent, liquefied gas diluent, solid diluent, or other suitable aid, for example, a surfactant such as emulsifier, dispersant, or foaming agent. The composition for controlling nematode having effective ingredient and the above vehicles mixed therein can be used after it is prepared in various formulations that are known in the field of pesticides, and, for producing a preparation, any method for producing a preparation that is typically used in the field of pesticides can be employed.

The composition for controlling nematode of the present invention can be preferably prepared as a formulation like wettable agent, granule, powder, emulsion, spray, aerosol, capsule, and gel, and it is preferably provided as a contact agent like a donut-like formulation for having buoyancy of a preparation.

The present invention further provides a method for controlling nematode by treating a plant or soil with the composition for controlling nematode.

By treating a plant or an area in need of control with the composition for controlling nematode of the present invention, which is formulated as above, root knot nematodes can be controlled. The preferred method is to have control by applying the composition for control such that it can be in direct contact with root knot nematodes, and a treatment method by mixing in soil or a method of spraying directly on plants is preferable.

The present invention still furthermore provides a method for producing a grammicin compound of the above chemical formula 1 including carrying out stationary culture of a *Xylaria grammica* strain in PDB (Potato dextrose broth) medium containing 4 to 23 g/l glucose.

According to the method of one embodiment of the present invention, content of the glucose contained in the PDB medium can be preferably 4 to 23 g/l, more preferably 10 to 20 g/l, and most preferably 20 g/l, but it is not limited thereto.

The grammicin compound of the present invention may be a compound which has been isolated from a *Xylaria grammica* strain. It is preferably a compound isolated from the *Xylaria grammica* strain with deposition number of KCTC13121BP, more preferably a compound isolated from culture broth of a *Xylaria grammica* strain, and most preferably a compound isolated from an ethyl acetate fraction of a culture solution of a *Xylaria grammica* strain, but it is not limited thereto.

With regard to the composition for controlling nematode according to the present invention, the nematodes are preferably root knot nematode (*Meloidogyne* sp.), and the root knot nematode (*Meloidogyne* spp.) may be more preferably sweet potato root knot nematode (*Meloidogyne incognita*), carrot root knot nematode (*Meloidogyne hapla*), Java root knot nematode (*Meloidogyne javanica*), peanut root knot nematode (*Meloidogyne arenaria*) or tomato root knot nematode (*Meloidogyne incognita*), and most preferably sweet potato root knot nematode (*Meloidogyne incognita*) or carrot root knot nematode (*Meloidogyne hapla*) strain, but it is not limited thereto.

Hereinbelow, the present invention will be described in detail with reference to the examples. However, it should be understood that the following examples are given only for the purpose of exemplification and it is evident that the scope of the present invention is not limited to the following examples.

EXAMPLES

Example 1

Mortality and Egg Hatching Inhibiting Activity of Each Solvent Fraction of Fungal Culture Filtrate

*Xylaria grammica* was subjected to stationary culture in potato dextrose agar (PDA) for 7 days at 25° C. Five pieces of fungal bodies were collected from an edge of the vigorously growing *Xylaria grammica* using a cork borer with diameter of 8 mm, and, after inoculation to a potato dextrose liquid broth (PDB) medium (500 ml conical flask, 100 ml medium), they were subjected to stationary culture for 14 days at 25° C. After 14 days, hypha was removed by using 4 layer gauze, and thus only the culture filtrate was obtained.

Thus-obtained culture filtrate (500 ml) was subjected, 2 times in turn, to fractionation extraction using ethyl acetate and 70% butanol in the same volume as the filtrate. Three fraction layers that are obtained by solvent fractionation were concentrated under reduced pressure so that 199.2 mg was obtained for ethyl acetate layer, 485.3 mg was obtained for butanol layer, and 14,933.7 mg was obtained for aqueous layer. Those fraction layers were examined in terms of the mortality against root knot nematode larva.

Specifically, the ethyl acetate extract and butanol extract of *Xylaria grammica* as prepared above were dissolved in methanol and the aqueous layer was dissolved in water, each at the concentration which is 100 times higher than the treatment concentration. The three layers were finally applied at concentrations of 15.6, 31.3, 62.5, 125, 250, 500, or 1,000 μg/ml. As a control group, treatment with 1% acetone and methanol was carried out, and, after the treatment, the 96-well plate was shaken for 30 seconds so that the test compound is mixed well. Thereafter, the plate was added to a plastic container having relative humidity of 100% and stored at room temperature. To obtain eggs of a root knot nematode from roots of tomato infected by root knot nematode, plant roots were washed with tap water to remove adhering soil and cut into 1 cm pieces. Eggs were extracted in 0.5% sodium hypochlorite solution for 1 min and collected by passage through 45 and 25 μm sieves. Second-stage juveniles (J2) were allowed to hatch in modified Baermann funnels at 20° C.

Ninety nine μl of 50 $2^{nd}$ stage juveniles of sweet potato root knot nematode were added to each well of a 96-well plate, and then, according to a treatment of 1% solvent extract, the final volume per well was adjusted to 100 μl.

After the treatment with a test compound, the 96-well plate was shaken for 30 seconds so as to have favorable mixing of the test compound, and, after addition to a plastic container having relative humidity of 100%, the plate was kept at room temperature. 72 Hours after the treatment with a test compound, mortality was determined under an optical inverted microscope by using the equation shown below. As for the mortality, the linear nematode showing no movement was taken as dead nematode, the nematode showing movement of flexible curve was taken as live nematode, and the mortality was examined using the following equation.

Mortality (%)=[Mortality percentage in treatment−mortality percentage of negative control/(100−mortality percentage in negative control)]×100

Figure 1:
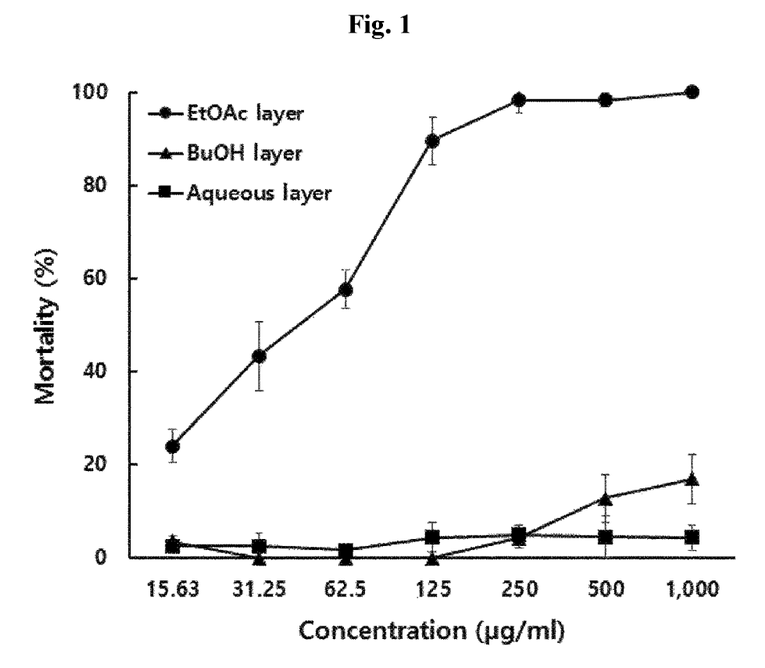
FIG. 1 shows the mortality of three organic solvent-fractionated layers against 2nd stage juveniles of sweet potato root knot nematode, in which the three organic solvent-fractionated layers have been obtained from an extract extracted from culture filtrate of *Xylaria grammica*; EtOAC: ethyl acetate, BuOH: butyl alcohol, and Aqueous: water.

As a result, as it is illustrated in FIG. 1, the mortality of 80% or higher was shown from the ethyl acetate layer at a concentration of 125 μg/ml or higher while it shows the mortality of 57.6% at a concentration of 62.5 μg/ml. At a concentration of 15.6 μg/ml, which is the lowest concentration, the mortality of 24.1% was shown. On the other hand, absolutely no activity was shown from the butanol layer or aqueous layer. As such, by using the ethyl acetate layer exhibiting the highest activity, following separation of a nematicidal compound was carried out.

Example 2

Separation of Nematicidal Compound

Figure 2:
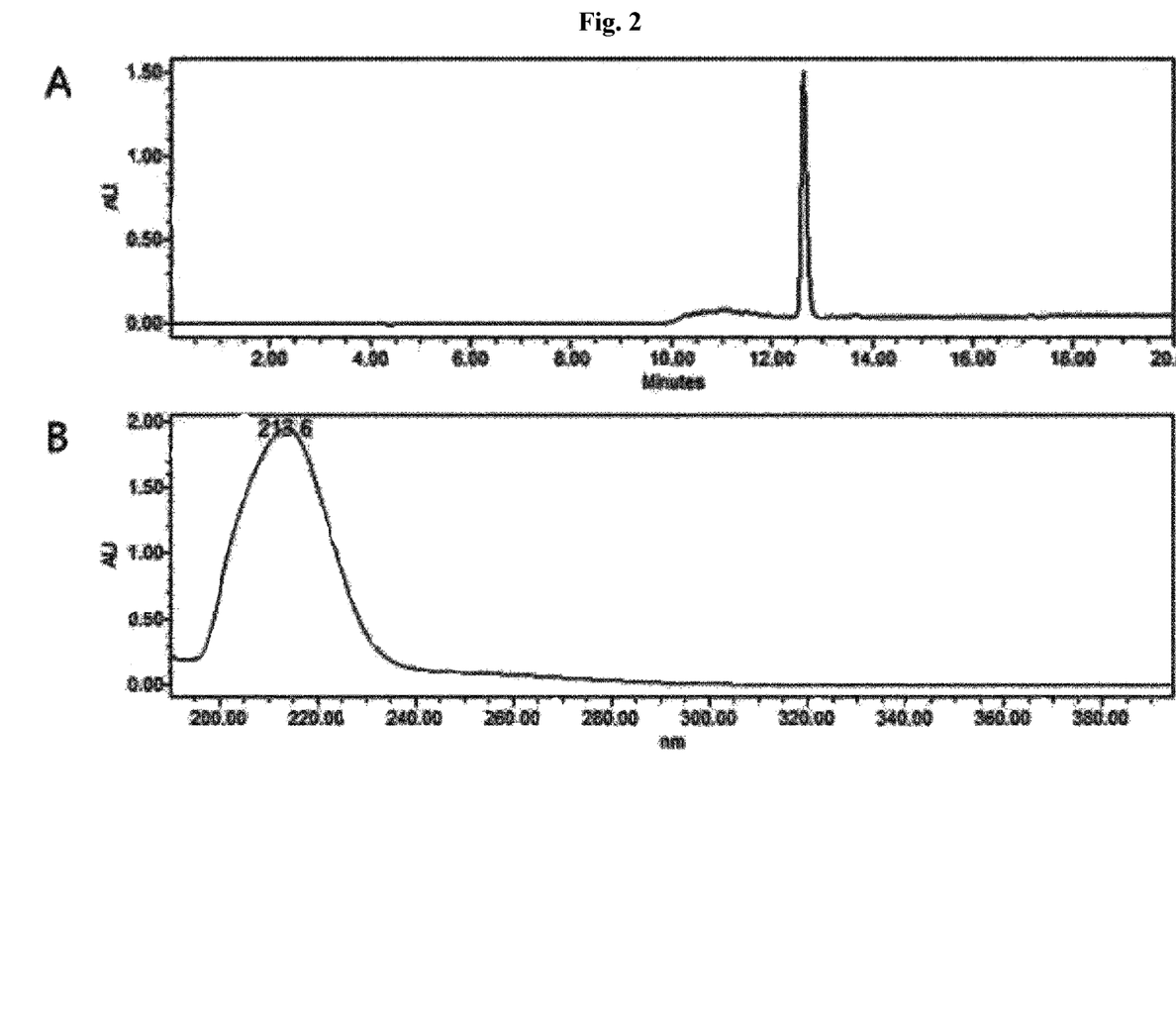
FIG. 2 shows chromatogram (A) and maximum absorbance of a nematicidal compound which has been isolated from *Xylaria grammica* (B).

To isolate an active compound from the ethyl acetate layer, the fungus was incubated according to the above method and more ethyl acetate layer was collected. After that, the ethyl acetate extract (703.2 mg) was loaded onto a silica gel column and then eluted with solvents of chloroform:methanol (93:7 v/v). Each fraction obtained by using a silica gel column was dissolved in methanol at a concentration of 10 mg/ml, and then tested for the nematicidal activity at a concentration of 200 μg/ml in 96-well plate. The untreated group was applied only with methanol. Fractions exhibiting the mortality against $2^{nd}$ stage juveniles of root knot nematode were collected and concentrated under reduced pressure to obtain an residue of 220.3 mg. The obtained residue (20 mg) was applied onto a Sep-Pak C18 reverse phase column. Elution of column was started with water, and, by increasing methanol content, final elution with 100% methanol was carried out. As a result, it was shown that the single compound (8.4 mg) eluted at water:methanol (9:1 v/v) condition is the same as the single compound (2.1 mg) eluted at water:methanol (8:2 v/v) condition, and thus two fractions were combined with each other. In order to determine the purity of isolated compound, HPLC analysis was carried out. As a column, a C18 reverse phase column (Atlantis T3, 5 μm, 4.6×250 mm, Waters, Co., Ireland) was used and, as a solvent, water containing 0.1% acetic acid and acetonitrile containing 0.1% acetic acid were used, and while increasing the portion of the organic solvent over 20 minutes, i.e., 0% methanol to 75% methanol, the analysis was carried out. As a result, one peak in the HPLC chromatogram at 12.7 minutes as shown in FIG. 2 appeared to confirm its purity.

Example 3

Structure Determination of the Purified Compound

The chemical structure of the purified was determined by EI-MS and $^1$H-$^{13}$C NMR. As a result of EI-MS analysis, [M]$^+$ value of m/z 154 was detected from the nematicidally active compound, and, based on NMR analysis, it was confirmed to have the molecular formula of $C_7H_6O_4$ as illustrated in A of FIG. 3. The nematicidally active compound was observed with 7 carbons from a $^{13}$C-NMR spectrum. 5 Carbons has a methine structure, and remaining 2 carbons are tetravalent carbons corresponding to δ 164.90 of number 9 and δ 169.58 of number 2. In the $^1$H-NMR spectrum, the hydrogen with δ 5.28 is connected to the number 4 carbon, and, according to the COSY analysis, hydrogens of δ 5.28, 4.98, 6.38 are connected to one another. The $^1$H and $^{13}$C-NMR data of purified compound are summarized in the following Table 2. Based on those spectrophotometric data, the nematicidally active compound produced by *Xylaria grammica* strain was identified as grammicin. In B of FIG. 3, structure of patulin as one type of toxins produced by fungus is shown, and grammicin is an isomer of patulin.

TABLE 1

$^1$H and $^{13}$C-NMR data of grammicin

| | Grammicin | |
|---|---|---|
| Position | $\delta_H$ (mult; J, Hz) | $\delta_C$ |
| 2 | — | 169.58, C |
| 3 | 6.20 (1H, s) | 115.46, C |
| 4 | 5.28 (1H, d) | 63.15, C |
| 5 | 4.98 (1H, dd) | 103.92, C |
| 6 | 6.38 (1H, d) | 142.26, C |
| 8 | 6.10 (1H, s) | 97.54, C |
| 9 | — | 164.90, C |
| 4-OH | 3.02 (1H, s) | |

Example 4

Mortality Against $2^{nd}$ Stage Juveniles and Egg Hatching Inhibitory Activity of the Purified Compound To determine the mortality and activity of inhibiting egg hatching of the purified compound, the compound was dissolved in methanol and trans-cinnamaldehyde as a control agent was dissolved in ethanol and used for the experiment. All test compounds were prepared at a concentration which is 100 times higher than the treatment concentration, and the mortality against 2nd stage juveniles of sweet potato root knot nematode (*M. incognita*) or carrot root knot nematode (*M. hapla*) was examined at the concentration level of 1.56 to 100 μg/ml. Furthermore, the activity of inhibiting egg hatching of sweet potato root knot nematode (*M. incognita*) was also examined at the same concentration. As a non-treatment group, 1% methanol and ethanol were used, and, according to the method explained above, the mortality and activity of inhibiting egg hatching were examined. The experiments were carried out in triplicate. The mortality was determined 3 days after the treatment of a test compound while the rate of inhibiting egg hatching was determined 14 days after the treatment of a test compound. The rate of inhibiting egg hatching was calculated based on the following equation.

Egg hatching inhibitory activity (%)=[(C−T)/C]×100,

C=Egg hatching rate of control group*, T=Egg hatching rate of treatment group

*Egg hatching rate (%)=Number of juveniles/[Number of egg+Number of juveniles]×100

Figure 4:
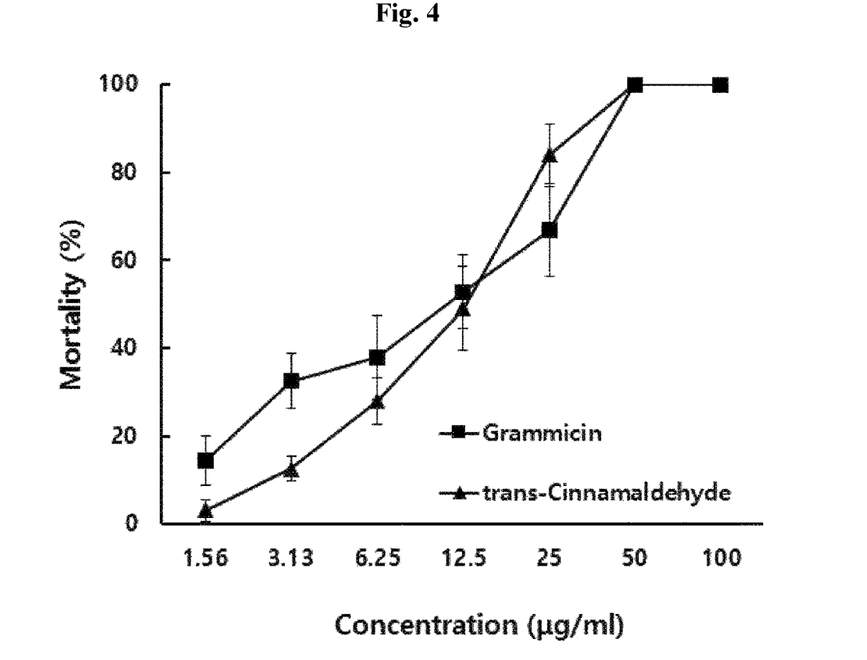
FIG. 4 shows the mortality of grammicin isolated from an extract of culture filtrate of *Xylaria grammica* and trans-cinnamaldehyde as a control agent against 2nd stage juveniles of sweet potato root knot nematode (*M. incognita*).
Figure 5:
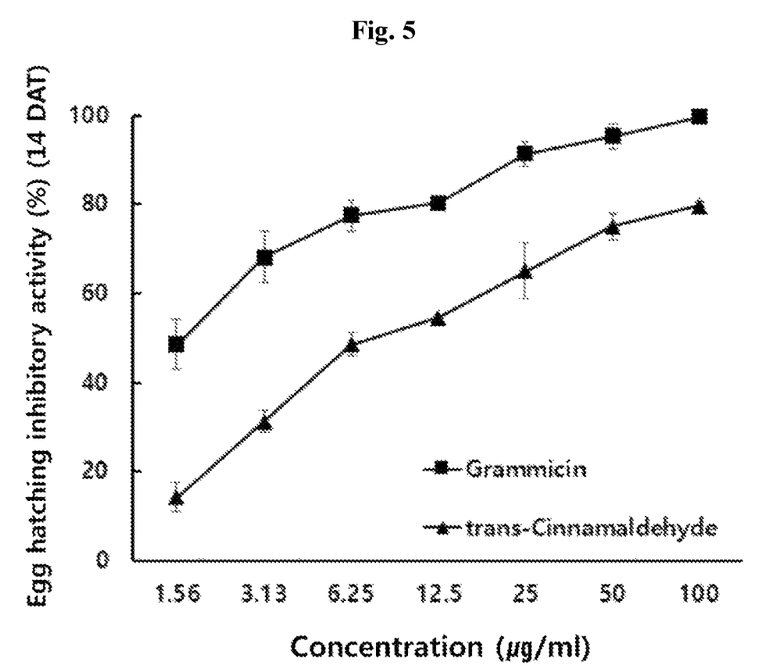
FIG. 5 shows the egg hatching inhibition rate of grammicin isolated from an extract of culture filtrate of *Xylaria grammica* and trans-cinnamaldehyde as a control agent against eggs of sweet potato root knot nematode (*M. incognita*).

As a result, the mortality of active compound against 2nd stage juveniles of sweet potato root knot nematode (*M. incognita*) was 52.8% mortality at concentration of 12.5 µg/ml and 100% mortality at concentration of 50 µg/ml as they are shown in FIG. 4. The results obtained by expressing those values in terms of $LC_{50}$ are summarized in the following Table 2, together with the results from carrot root knot nematode (*M. hapla*). The rate of inhibiting egg hatching of sweet potato root knot nematode (*M. incognita*) was 68.2% at concentration of 3.1 µg/ml and 91.4% at concentration of 25 µg/ml as they are shown in FIG. 5. Thus, it was demonstrated that the activity of inhibiting egg hatching by the active compound is significantly higher than trans-cinnamaldehyde, which has been used as a control group (i.e., 31.3% at concentration of 3.1 µg/ml and 65.0% at concentration of 25 µg/ml).

Figure 6:
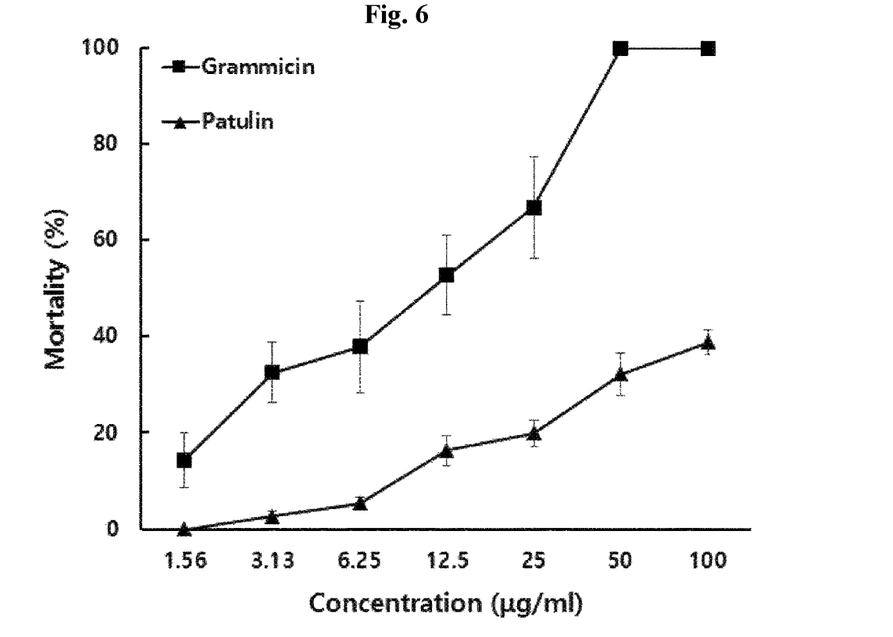
FIG. 6 shows the mortality of grammicin isolated from an extract of culture filtrate of *Xylaria grammica* and patulin as a control agent against 2nd stage juveniles of carrot root knot nematode (*M. hapla*).

Furthermore, the mortality of active compound against 2nd stage juveniles of carrot root knot nematode (*M. hapla*) was 62.4% mortality at concentration of 25 µg/ml and 100% mortality at concentration of 50 µg/ml as they are shown in FIG. 6. Accordingly, it was confirmed that grammicin as an active compound isolated by the present invention has a mortality against 2nd stage juveniles of sweet potato root knot nematode (*M. incognita*) and carrot root knot nematode (*M. hapla*), and it also has an activity of inhibiting the egg hatching of sweet potato root knot nematode (*M. incognita*).

TABLE 2

$LC_{50}$ values of grammicin as nematicidal compound isolated from *Xylaria grammica* strain and trans-cinnamaldehyde as control agent against sweet potato root knot nematode (*M. incognita*) and carrot root knot nematode (*Meloidogyne hapla*)

| Treatment | $LC_{50}$ (µg/ml) | | | |
|---|---|---|---|---|
| | *M. incognita* 72 h | $R^2$ | *M. hapla* 72 h | $R^2$ |
| Grammicin | 15.95 | 0.94 | 3.12 | 0.96 |
| trans-Cinnamaldehyde | 18.34 | 0.92 | 8.56 | 0.98 |

Example 6

Figure 3:
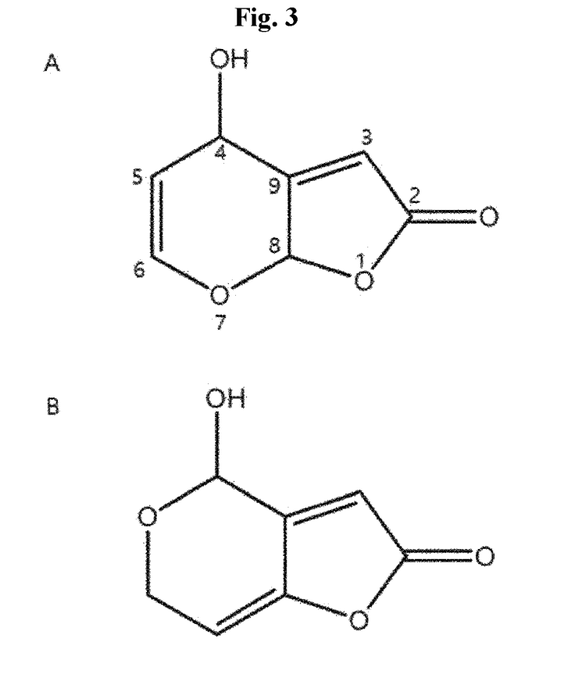
FIG. 3 shows chemical structure of grammicin, which is a nematicidally active compound isolated from an ethyl acetate extract of culture filtrate of *Xylaria grammica* (A), and patulin as an isomer of grammicin (B).
Figure 7:
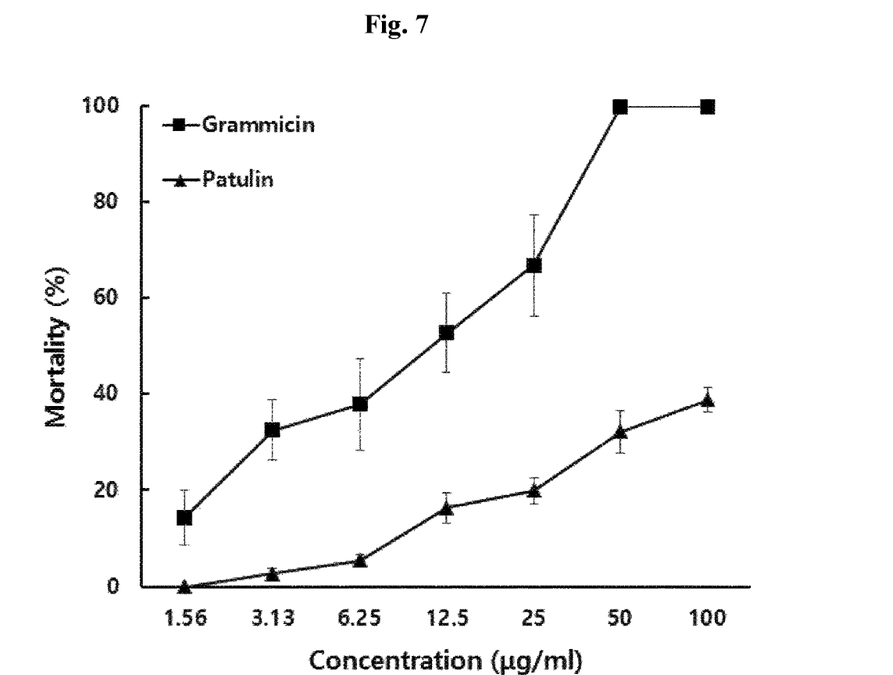
FIG. 7 shows the mortality of grammicin isolated from an extract of culture filtrate of *Xylaria grammica* and patulin as an isomer of grammicin against 2nd stage juveniles of sweet potato root knot nematode (*M. incognita*).

Comparison of Mortality Between Grammicin as the Purified Nematicidal Compound and Patulin as Isomer of Grammicin Patulin has a chemical structure of B of FIG. 3, and it is an isomer of grammicin, which is a nematicidal compound isolated in the above. To compare the mortality between grammicin and patulin, both test compounds were dissolved in methanol and, as a control agent, trans-cinnamaldehyde was used as it has been used for the previous experiments. As illustrated in FIG. 4, grammicin shows 100% mortality at minimum concentration of 50 µg/ml. Thus, from a concentration of 100 µg/ml, which is 2 times higher than 50 µg/ml, to concentrations of 50, 25, 12.5, 6.25, 3.12, and 1.56 µg/ml, the mortality against 2nd stage juveniles of sweet potato root knot nematode (*M. incognita*) was examined. As a result, it was shown that, like grammicin, patulin also exhibits higher activity against 2nd stage juveniles of sweet potato root knot nematode (*M. incognita*) in accordance with an increase in the concentration as it is illustrated in FIG. 7. However, at the highest concentration tested, i.e., 100 µg/ml, it exhibits the mortality that is as low as 38.74%. As such, it was found that patulin has a very weak mortality against 2nd stage juveniles of root knot nematode compared to grammicin, even though it is an isomer of grammicin.

Example 7

Comparison of Cytotoxicity for Colon Cancer Cell SW.71 Between Grammicin and Patulin as Isomer of Grammicin In order to have comparison of human cytotoxicity for colon cancer cell SW.71 between grammicin which has been purified as nematicidal compound in pure form from culture extract of *Xylaria grammica* and patulin as an isomer of grammicin, MTT cell viability assay was carried out. The colon cancer cell SW.71 as a cell line used for the experiment was kept in –196° C. liquid nitrogen tank until use. The colon cancer cell SW.71 was added, in RPMI-1640 (Life Technologies Inc., USA) medium, with 10% FBS (fetal bovine serum, Gibco) and 1% penicillin-streptomycin, cultured for 72 hours in an incubator at condition of 37° C., 5% $CO_2$, and then used. As for the MTT reagent, thiazolyl blue tetrazolium bromide was used, and, after dissolving it in PBS (phosphate buffer saline) to have final concentration of 5 mg/ml, it was kept at 4° C. under light-shielding condition. The colon cancer cell SW.71 was inoculated, in an amount of 130 µl, to a 96-well plate to have concentration of $5 \times 10^3$ or $1 \times 10^4$ cells/well. Grammicin and patulin were diluted in DMEM medium to have final concentration of 10, 5, 1, 0.5, or 0.1 µg/ml, and then added to each well in an amount of 14.5 µl. After culturing the cells for 24 hours, the MTT solution was added in an amount of 14.5 µl for each well followed by culture for 2 hours or longer at 37° C. The medium was carefully removed and DMSO was added in an amount of 108.5 µl per well to terminate the reaction followed by stirring using a plate shaker for 30 minutes at room temperature, dark conditions. Thereafter, by using a microplate ELISA reader, absorbance at a wavelength of 540 nm was measured, and the cell viability after culture for 24 hours was examined. For the non-treatment group, 1% MeOH was added to a DMEM medium. All the experiments were repeated in triplicate.

Figure 8:
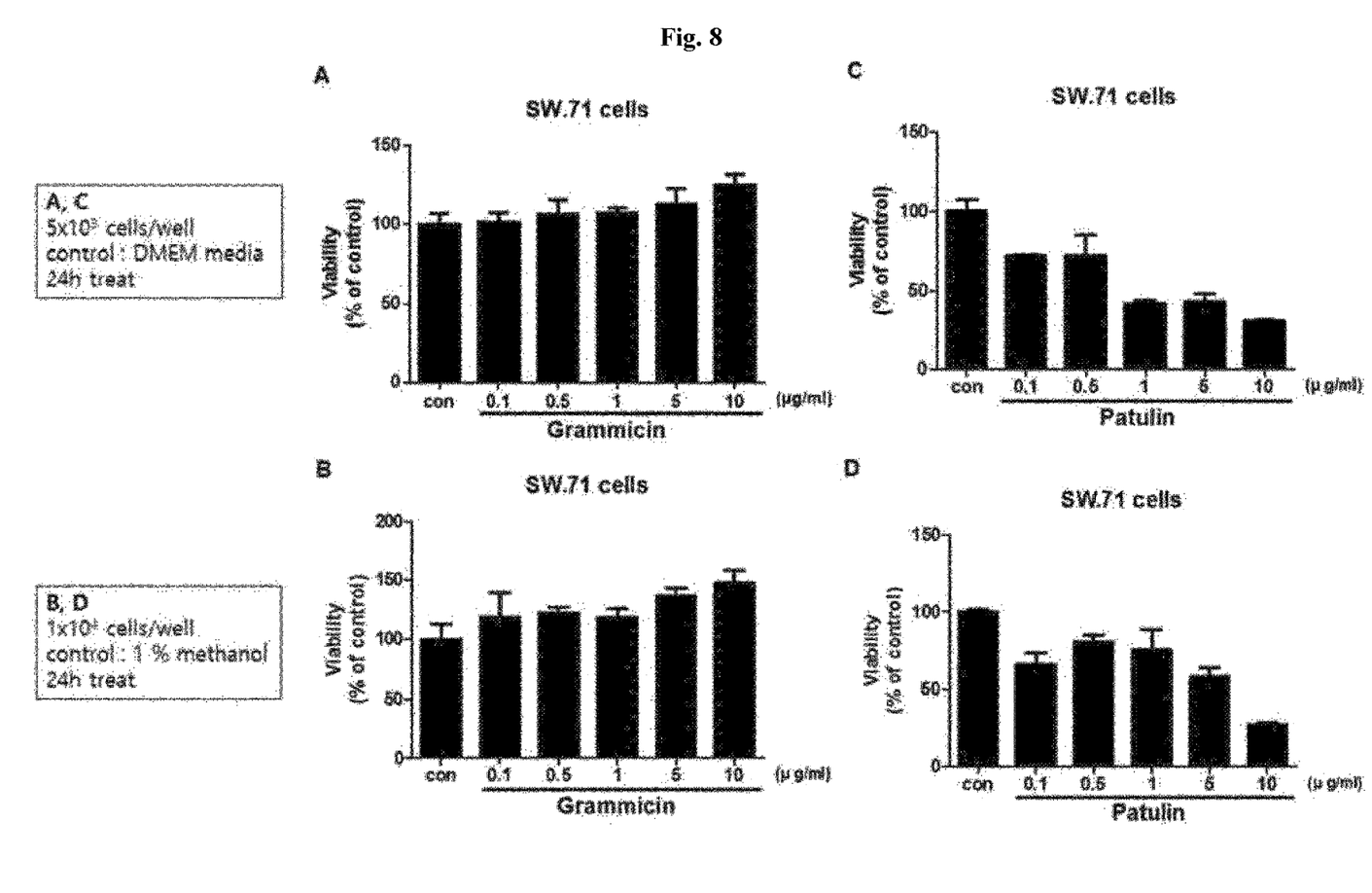
FIG. 8 shows the human cytotoxicity of grammicin isolated from an extract of culture filtrate of *Xylaria grammica* and patulin as an isomer of grammicin against colon cancer cells SW.71 strain.

As a result, the grammicin treatment group showed, at the test concentration, no cytotoxicity for both inoculation groups of $5 \times 10^3$ and $1 \times 10^4$ cells/well as it can be recognized from FIG. 8. However, in both treatments, the patulin treatment group showed higher cytotoxicity in accordance with an increase in the concentration. With regard to the patulin, the 0.1, 0.5, 1, 5, and 10 µg/ml treatment groups showed, in the treatment of $5 \times 10^3$ cells/well, cell viability of 72.2%, 72.1%, 42.1%, 43.5%, and 31.4%, respectively, compared to the non-treatment group. In the treatment of $1 \times 10^4$ cells/well, cell viability of 66.2%, 80.5%, 75.3%, 58.4%, or 27.6% was shown compared to the non-treatment group. As such, it was demonstrated that grammicin has much stronger mortality than patulin, but it has much lower cell toxicity compared to patulin.

Example 8

Determination of Optimum Culture Conditions for Producing Grammicin by *Xylaria Grammica* EL 000614 Strain In the present invention, *Xylaria grammica* EL 000614 strain was always subjected to stationary culture (PDB, 25° C. condition). To enhance the production amount of grammicin as a nematicidally active compound produced by Xylaria grammica EL 000614 strain, the strain was cultured by modifying the medium composition. As a method of modification, glucose was added (5 g, 10 g, 20 g) to a previously used PDB medium (500 ml conical flask, 100 ml PDB medium) and stationary culture was continues for 7 days, 14 days, or 21 days at 25° C. condition. Furthermore, to investigate the influence exhibited by stationary culture or shaking culture on production amount of grammicin, the strain was inoculated to PDB medium and cultured by the two different methods.

To determine the grammicin content in culture filtrate, the culture broth was filtered through 4 layer gauze to remove hypha. Thus-obtained culture filtrate was diluted by 1/10 and subjected to HPLC analysis. As a column, a C18 reverse phase column (Atlantis T3, 5 μm, 4.6×250 mm, Waters, Co., Ireland) was used and, as a solvent, water containing 0.1% acetic acid and acetonitrile containing 0.1% acetic acid were used, and while increasing the portion of the organic solvent over 45 minutes, i.e., 0% methanol to 100% methanol, the analysis was carried out. As a standard compound, grammicin solutions of 125, 250, 500, and 1,000 μg/ml were used. After that, a standard calibration curve was established, and, by incorporating the area of grammicin peak of each test compound into the calibration curve, the grammicin content in culture filtrate was obtained.

Figure 9:
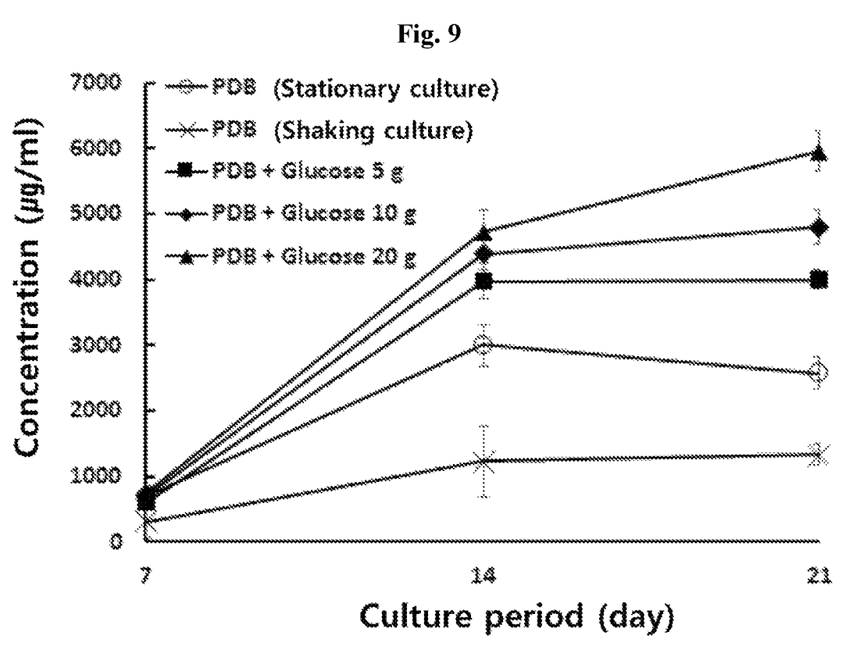
FIG. 9 shows the result of examining the production amount of grammicin by *Xylaria grammica* in various media and various conditions.

As a result, it was shown like those illustrated in FIG. 9 that, from the medium having 20 g of glucose added to PDB medium, grammicin was produced in an amount of 739.78, 4,720.57, or 5,960.54 μg/ml on Day 7, Day 14, and Day 21 of culture, respectively. From the medium having 10 g of glucose added to PDB medium, grammicin was produced in an amount of 700.82, 4389.52, 4797.34 μg/ml on Day 7, Day 14, and Day 21 of culture, respectively. From the medium having 5 g of glucose added to PDB medium, grammicin was produced in an amount of 611.23, 3977.03, 4004.7 μg/ml on Day 7, Day 14, and Day 21 of culture, respectively. As such, it was found that grammicin is produced in the largest amount in a medium with 20 g glucose. Furthermore, as a result of carrying out stationary culture in pure PDB medium, grammicin was produced in an amount of 692.84, 3006.97, 2579.29 μg/ml on Day 7, Day 14, and Day 21 of culture, respectively. On the other hand, as a result of carrying out shaking culture in pure PDB medium, grammicin was produced in an amount of 310.03, 1233.52, 1327.35 μg/ml on Day 7, Day 14, and Day 21 of culture, respectively. Thus, as a result of those experiments, it was confirmed that the grammicin production by *Xylaria grammica* EL 000614 strain in PDB medium is higher in stationary culture compared to shaking culture, and also even larger amount of grammicin can be produced when glucose is further added to PDB medium.

The invention claimed is:

1. A method for controlling nematode, the method comprising:
  treating a plant or soil with a composition comprising a compound of Formula 1 or an agriculturally acceptable salt thereof:

[Formula 1]

2. The method of claim 1, wherein the compound is isolated from an *Xylaria grammica* strain.

3. The method of claim 1, wherein the nematode is root knot nematode.

4. The method of claim 1, wherein the nematode is sweet potato root knot nematode (*Meloidogyne incognita*), carrot root knot nematode (*Meloidogyne hapla*), Java root knot nematode (*Meloidogyne javanica*), peanut root knot nematode (*Meloidogyne arenaria*) or tomato root knot nematode (*Meloidogyne incognita*).

5. The method of claim 1, wherein the composition further comprises a nematicidally active compound.

6. The method of claim 5, wherein the nematicidally active compound is selected from the group consisting of an avermectin-based nematicidally active compound, morantel tartrate, mesulfenfos, levamisol, and a combination thereof.

7. The method of claim 1, wherein the composition further comprises an agrochemically acceptable carrier or a diluent.

8. The method of claim 1, wherein the composition is formulated as a wettable agent, a granule, a powder, an emulsion, a spray, an aerosol, a capsule, or a gel.

9. The method of claim 2, wherein the *Xylaria grammica* strain is the strain deposited with Korea Research Institute of Bioscience and Biotechnology under the accession number of KCTC 13121BP.

\* \* \* \* \*